(12) United States Patent
Ropars et al.

(10) Patent No.: US 9,994,873 B2
(45) Date of Patent: Jun. 12, 2018

(54) PROCESS FOR THE PRODUCTION OF ALCOHOLS AND/OR SOLVENTS FROM LIGNOCELLULOSIC BIOMASS WITH ACID RECYCLE OF SOLID RESIDUES

(75) Inventors: Marcel Ropars, Palaiseau (FR); Caroline Aymard, Lyons (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 1630 days.

(21) Appl. No.: 13/320,390

(22) PCT Filed: May 6, 2010

(86) PCT No.: PCT/FR2010/000350
§ 371 (c)(1),
(2), (4) Date: Dec. 5, 2011

(87) PCT Pub. No.: WO2010/130888
PCT Pub. Date: Nov. 18, 2010

(65) Prior Publication Data
US 2012/0100585 A1  Apr. 26, 2012

(30) Foreign Application Priority Data
May 15, 2009  (FR) .................................. 09 02347

(51) Int. Cl.
C12P 7/28 (2006.01)
C12P 7/10 (2006.01)
C12P 7/16 (2006.01)

(52) U.S. Cl.
CPC ...... *C12P 7/10* (2013.01); *C12P 7/16* (2013.01); *C12P 7/28* (2013.01); *C12P 2201/00* (2013.01); *C12P 2203/00* (2013.01); *Y02E 50/10* (2013.01); *Y02E 50/16* (2013.01); *Y02P 20/582* (2015.11)

(58) Field of Classification Search
None
See application file for complete search history.

(56) References Cited

U.S. PATENT DOCUMENTS

2008/0032344 A1  2/2008 Fallavollita
2009/0035826 A1* 2/2009 Tolan et al. ............ 435/99
2010/0273228 A1 10/2010 Sant'Anna et al.

FOREIGN PATENT DOCUMENTS

| FR | 2 903 119 A1 | 1/2008 |
| WO | WO 2004/113549 A1 | 12/2004 |
| WO | WO 2008/017145 A1 | 2/2008 |
| WO | WO 2009/004273 A1 | 1/2009 |

OTHER PUBLICATIONS

Aleksandrova et al. "Changes in the Structural Composition of Hardwood Kraft Pulp during Bleaching" Applied Biochemistry and Microbiology, vol. 36, No. 3, 2000, pp. 245-249.*
Mimms et al. "Kraft Pulping" TAPPI Press, 1993, pp. 58-73.*
International Search Report of PCT/FR2010/000350 (dated Dec. 16, 2010), 7pgs.
International Search Report of PCT/FR2010/000350 (dated Dec. 16, 2010).
F. Carvalheiro et al., "Hemicellulose Biorefineries: A Review on Biomass Pretreatments", Journal of Scientific & Industrial Research, vol. 67, No. 11 (Nov. 1, 2008) pp. 849-864.

* cited by examiner

*Primary Examiner* — Thane Underdahl
(74) *Attorney, Agent, or Firm* — Millen White Zelano and Branigan, PC; John Sopp

(57) ABSTRACT

The present invention describes a process for the production of alcohols and/or solvents from a cellulosic or lignocellulosic substrate, comprising at least the following steps:

a step A for alkaline pre-treatment of said substrate, comprising a step for heating in the presence of an alkaline chemical reagent and an optional washing step;

a step B constituted by a step for adjusting the pH and a step for enzymatic hydrolysis of the pre-treated substrate, at the end of which a hydrolysate is obtained constituted by a liquid phase containing sugars and a solid residue;

a step for alcoholic fermentation of the hydrolysate obtained;

a step for separation/purification (step C2) at the end of which one or more purified alcohols and/or solvents are obtained;

a step for extracting the solid residue;

a step D for acid digestion of at least a fraction of the extracted solid residue, at the end of which a portion or all of the product obtained is recycled to step B.

11 Claims, 2 Drawing Sheets

PROCESS FOR THE PRODUCTION OF ALCOHOLS AND/OR SOLVENTS FROM LIGNOCELLULOSIC BIOMASS WITH ACID RECYCLE OF SOLID RESIDUES

FIELD OF THE INVENTION

The context of the present invention is in so-called "second generation" processes for the production of alcohols and/or solvents from lignocellulosic biomass. More particularly, it concerns a process for the production of ethanol and/or an acetone-butanol-ethanol mixture (also termed an ABE mixture).

PRIOR ART

Lignocellulosic biomass represents one of the most abundant renewable sources on the planet. The substrates under consideration are highly varied since they concern both ligneous substrates (deciduous and coniferous), agricultural by-products (straw) or those from industries generating lignocellulosic waste (agroalimentary or paper industries).

Lignocellulosic biomass is composed of three principal polymers: cellulose (35% to 50%), hemicellulose (20% to 30%), which is a polysaccharide essentially constituted by pentoses and hexoses, and lignin (15% to 25%), which is a polymer with a complex structure and a high molecular weight composed of aromatic alcohols linked via ether bonds.

Those various molecules are responsible for the intrinsic properties of the plant wall and are organized into a complex network.

Cellulose and possibly hemicelluloses are the targets for enzymatic hydrolysis, but they are not directly accessible to enzymes. For this reason, such substrates have to undergo a pre-treatment preceding the enzymatic hydrolysis step. The pre-treatment is intended to modify the physical and physico-chemical properties of the lignocellulosic material with a view to improving the accessibility of the cellulose trapped in the matrix of lignin and hemicellulose.

Many techniques exist for carrying out such a pre-treatment: acid digestion, alkaline digestion, steam explosion, organosolve processes, etc. The efficiency of the pre-treatment is measured both by the material balance at the end of the pre-treatment (recovery yield for sugars in the form of soluble monomers or oligomers or solid polymers) and also by the susceptibility of the cellulosic and hemicellulosic residues to hydrolysis.

Pre-treatments under acid conditions have a tendency to form degradation products of the sugars pentose and hexose (for example furfural, 5-HMF) as well as many other products such as organic acids, aldehydes or phenolic alcohols, which are also derived from the acid degradation of sugars and partially dissolved lignin. Depending on their concentration, these degradation products can inhibit fermentation organisms. The formation of such degradation products increases with the severity of the pre-treatment (heat, retention time, acidity). The hemicellulose of the lignocellulosic substrate is hydrolyzed very readily under acid conditions and at high temperature. Nevertheless, a pre-treatment that is not severe enough risks not acting sufficiently on the lignin present and thus reducing the susceptibility of the substrate to enzymatic hydrolysis.

Pre-treatments in alkaline media have the advantage of not generating degradation products. They represent a viable alternative to acid pre-treatments, although their cost, in particular for the chemical products employed, is now higher.

There is currently no leading acid, alkali or other pre-treatment on the technico-economic front (Eggeman et al, Bioresource Technology 96 (2005), 2019-2025).

In order to convert the substrate into alcohols and/or solvents, enzymatic hydrolysis is carried out on the pre-treated substrate. The lignin, cellulose, and hemicellulose fractions present in the substrate depend on the pre-treatment carried out. For alkaline pre-treatments, the solid is primarily constituted by cellulose and hemicelluloses.

Enzymatic hydrolysis is carried out at a pH in the range 4.5 to 5.5, preferably in the range 4.8 to 5.2. The feed from an alkaline pre-treatment must thus be neutralized and brought to the correct pH before it commences enzymatic hydrolysis.

Enzymatic hydrolysis is carried out with an enzymatic solution, usually produced from filamentous fungi such as *Trichoderma reeseii*, or occasionally *Aspergillus niger*. Those fungi secrete an "enzymatic cocktail" composed of several different enzymes, up to 50, such as CBHI, CBHII, for example, which are involved in the hydrolysis of cellulose, and xylanases which are involved in pentose hydrolysis. The exact composition of the cocktail depends on the strain of fungus used and the culture conditions. The cost of the enzymatic solution penalizes processes for converting lignocellulosic biomass by fermentation pathways; genetic research has been carried out on fungi in order to improve the enzymatic cocktail. However, the mechanisms involved are not very well known and genetic modifications to fungi are complex and delicate. The principal aim of that work has been to improve enzymatic hydrolysis of cellulose under economically reasonable conditions. For the moment, xylanase activities have not been studied in depth and are usually low.

One possibility for limiting the overall cost is to reduce the enzymatic load. The hydrolysis yield for cellulose and hemicelluloses is dependent on the operating conditions, in particular the quantity of enzymatic solution added. This dependency is not linear; a portion of the sugar polymers is readily hydrolysable following pre-treatment. For this reason, a small dose of enzymes can result in better upgrading of the expensive enzymatic solution (kg of hydrolysed sugars per kg of solution employed). However, this occurs to the detriment of the hydrolysis yield for the sugar polymers. It is important to note that the cost of the initial biomass makes a major contribution to the cost price of the end product because of the limited mass yields inherent to fermentation processes. As an example, the stoichiometric equation for the conversion of glucose to ethanol gives a maximum mass yield of 0.51 kg of ethanol per kilogram of glucose.

In contrast, maximum hydrolysis of the substrate would necessitate a very high dose of enzymes. It should be noted that certain pre-treatments and/or substrates produce pre-treated solids containing cellulose which is termed recalcitrant and which cannot be completely hydrolysed.

In order to be economically viable, a second generation process for the production of alcohols and/or solvents must be able to provide a compromise between the upgrade to the enzymatic solution and the upgrade to the biomass.

In this type of process, the enzymatic hydrolysis step is followed by alcoholic fermentation. At the end of these two steps, the desired products are obtained (alcohols and/or solvents) along with solid residues still containing polymers and sugars, in greater or lesser quantities depending on the performance of the enzymatic hydrolysis.

A great deal of research has been carried out into improving the upgrade of the lignocellulosic substrate at various stages of the biomass conversion process.

More particularly, the present invention proposes upgrading the solid residues obtained in this type of process, with a view to improving the overall mass balance and thus the economic viability of the process.

SUMMARY OF THE INVENTION

The present invention pertains to a process for the production of alcohols and/or solvents termed a second generation process, in which the lignocellulosic or cellulosic biomass undergoes an alkaline pre-treatment.

DETAILED DESCRIPTION OF THE INVENTION

Figure 1:
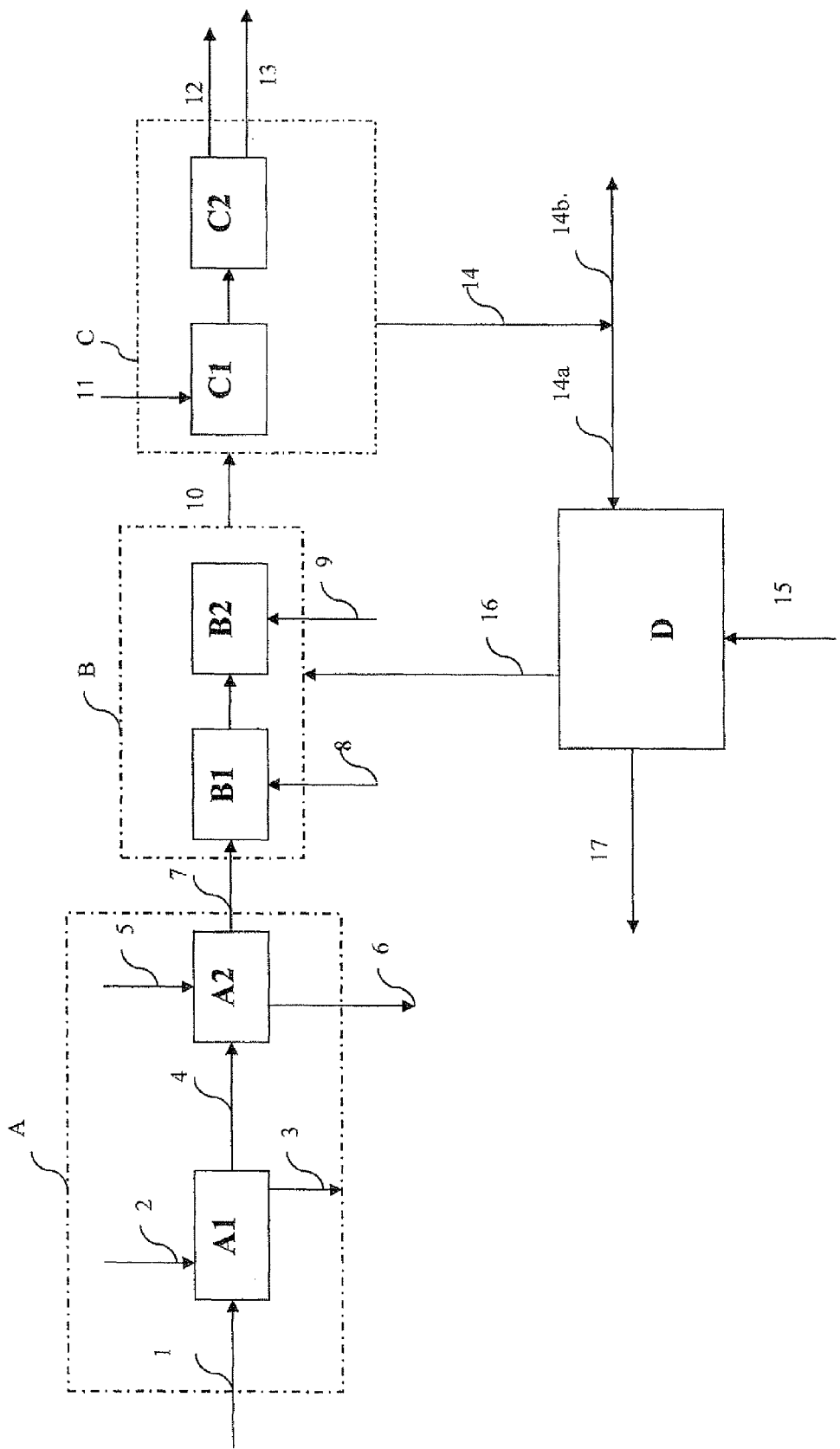
FIG. 1 is a diagrammatic representation of a device implementing a process for the production of alcohols and/or solvents, further comprising a step for recycling solid residues after acid digestion, in accordance with the present invention.

The present invention describes a process for the production of alcohols and/or solvents from a cellulosic or lignocellulosic substrate, comprising at least the following steps:
- a step for alkaline pre-treatment (step A) of said substrate, comprising a step for heating in the presence of an alkaline chemical reagent (step A1) and an optional washing step (step A2), at the end of which at least one pre-treated substrate is obtained;
- a step B constituted by a step for adjusting the pH to between 4.5 and 5.5 (step B1) and a step for enzymatic hydrolysis (step B2) of the pre-treated substrate using cellulolytic and/or hemicellulolytic enzymes, at the end of which a hydrolysate is obtained constituted by a liquid phase containing sugars and a solid residue;
- a step for alcoholic fermentation (step C1) of the hydrolysate obtained by an alcohol-producing microorganism;
- a step for separation/purification (step C2) at the end of which one or more purified alcohols and/or solvents are obtained;
- a step for extracting the solid residue;
- a step for acid digestion (step D) of at least a fraction of the extracted solid residue, at the end of which a portion or all of the product obtained is recycled to step B.

The process of the present invention can be used to improve the material yield and upgrade the solid residues obtained at the various steps of the process. Thus, the economic balance is more favorable.

The product from the acid digestion originating from the solid residues extracted after the various steps is advantageously used for the step for adjusting the pH necessary in order to carry out the enzymatic hydrolysis.

Thus, by carrying out the acid digestion step under less severe conditions, the hemicelluloses present in the insoluble solid residue are hydrolysed into monomeric sugars and dissolved. Few sugar degradation products are generated and the undigested cellulose present, also known as "recalcitrant cellulose", becomes more readily accessible to the cellulolytic enzymes. Usually, the cellulolytic cocktails such as those produced by $T.$ $reesei$ are not sufficiently rich in xylanase activities to obtain effective hydrolysis of the hemicelluloses. This acid hydrolysis under mild conditions is an interesting technical option, in particular for paper pulp, for example that from the Kraft process and "relatively rich in hemicelluloses", such as unbleached products.

By carrying out said acid digestion under severe conditions (concentration of acid, duration, temperature applied), it is possible to chemically hydrolyse all or nearly all of the recalcitrant cellulose in a first enzymatic hydrolysis. Under these severe conditions, the hemicelluloses are also chemically hydrolysed in their entirety; on the one hand, the pentose sugars are partially degraded to furfural, and on the other hand, hexose sugars are degraded to a slight extent to 5-HMF, levulinate and formate. Further, acid digestion of the lignin contributes to liberating phenolic products such as vanillic, coumaric, ferulic, or syringic acids/aldehydes, which will all contribute to protecting the quantity of sugars in the hydrolysate by rendering the medium more toxic for potential contaminants such as lactic bacteria.

The alkaline chemical pre-treatment carried out in step A is preferably a sodium sulphate pre-treatment, also known as the Kraft process, conventionally used in processes for the production of paper products, known as Kraft or "sulphate pulp", at the end of which paper pulp is obtained.

The alkaline chemical pre-treatment carried out in step A may also be an ammonia fiber explosion pre-treatment, also termed AFEX pre-treatment, or an ammonia recycle percolation pre-treatment, also termed ARP pre-treatment.

Step A1 of the process of the present invention is a step for digestion in the presence of an alkaline chemical reagent. This reagent is in the liquid or gas form, depending on the pre-treatment which is carried out.

The sodium sulphate or Kraft process is based on the use of sodium hydroxide and sodium sulphate. The chemical treatment of wood chips is carried out at 150-175° C. for a period of 1 to 7 hours depending on the substrate used. This Kraft paper pulp is produced from a very broad range of biomasses, but more particularly from coniferous arborescent species (softwoods such as spruce or pine) or deciduous species (hardwoods such as eucalyptus) or from agricultural lignocellulosic waste (straw from wheat, rice etc). They are partially delignified by cooking at high temperature in the presence of sodium hydroxide. This delignification is controlled by the operating parameters of the reactors. The cooking is carried out in a vertical reactor where the chips descend under gravity and encounter the various liquors from cooking. The sodium sulphide is prepared directly from sodium sulphate by combustion. During cooking, the sodium sulphide is hydrolyzed into sodium hydroxide, NaHS and $H_2S$. The various sulphur-containing compounds present react with the lignin to produce more readily soluble thiolignins. The liquor applied to the chips is termed white liquor. The liquor extracted from the reactor or digester containing the compounds eliminated from the wall is termed black liquor.

Following this alkaline pre-treatment, a pre-treated substrate is produced which is enriched in cellulose since it contains in the range 60% to 90% of cellulose and in the range 5% to 20% of hemicellulose.

Other alkaline pre-treatments have been studied on a laboratory scale with the aim of reducing the costs of this step when producing a fuel.

The ARP (ammonia recycle percolation) process is a pre-treatment process using ammonia in recycle mode. This type of process has in particular been described by Kim et al, 2003, Biores Technol 90 (2003), pp 39-47. The high temperature of the percolation results in partial dissolution of both the lignin and the hemicelluloses, then this solution is heated to recycle the ammonia and to recover the extracted lignin, for example for energy recovery, along with the soluble sugars derived from the hemicelluloses.

The AFEX (ammonia fiber explosion) process consists of introducing the lignocellulosic substrate into a high pressure digester in the presence of ammonia then causing an explosive decompression at the reactor outlet and then recycling the ammonia which is then in the gaseous form. This type of process has been described in particular by Teymouri et al, 2005, Biores Technol 96 (2005), pp 2014-2018. This process principally results in destructuring the biomass matrix, but there is no phase separation of the lignin, hemicellulose and cellulose compounds at the outlet from the treatment.

Other alkaline treatments are also being studied, in particular based on sodium hydroxide or lime; a non-exhaustive review has been provided by Ogier et al, 1999, Oil & Gas Science and Technology, IFP review, Vol 54 (1999), No 1, pp 67-94.

These alkaline pre-treatments may be combined with a mechanical action created, for example, in a twin screw extruder or a pulper.

Optional step A2 is a step consisting of washing the pre-treated substrate by introducing one or more wash liquids. This washing step may also be limited to a dilution step.

Step B1 for adjusting the pH of the pre-treated substrate, which has optionally been washed, is carried out by adding a pH correcting solution.

Preferably, the pH correcting solution is an acid solution.

Step B2 is the enzymatic hydrolysis step proper, and is carried out under mild conditions, at a temperature of the order of 45-50° C. and a pH of 4.5-5.5, preferably in the range 4.8 to 5.2. It is carried out using enzymes produced by a microorganism. Microorganisms such as fungi belonging to the genuses *Trichoderma, Aspergillus, Penicillium* or *Schizophyllum*, or anaerobic bacteria belonging, for example, to the genus *Clostridium*, produce these enzymes, in particular containing cellulases and hemicellulases, which are adapted to the intense hydrolysis of cellulose and hemicelluloses.

The microorganisms may be produced in an independent production line and may be carried out on-site or off-site.

Highly preferably, the microorganism used is *Trichoderma reesei*.

Advantageously, steps B1 and B2 are carried out simultaneously and the pH is adjusted in the enzymatic hydrolysis reactor.

Because of the alkaline pre-treatment carried out (step A), the susceptibility to enzymatic hydrolysis is excellent and the cellulose and hemicellulose polymers are dissolved into monomeric and/or oligomeric sugars with different degrees of polymerization by the action of the enzymes.

The hydrolysis conditions, principally the quantity of dry matter in the mixture to be hydrolysed and the quantity of enzymes used, results at the end of step B in partial hydrolysis, in the range 20% to 90%, of the cellulose of the pre-treated substrate into glucose, more particularly in the range 50% to 80%, as well as partial hydrolysis, between 20% and 90%, of the solid hemicelluloses of the pre-treated substrate, more preferably between 40% and 70%.

Step C1 is the fermentation step, using a microorganism, of the hydrolysate obtained after enzymatic hydrolysis. The fermentable sugars are thus transformed into alcohols and/or solvents by the yeasts. Fermentation is usually carried out at a temperature in the range 30° C. to 35° C. At the end of this step, a fermentation mash is obtained comprising material in suspension and a liquid phase which contains the product or products (alcohols and/or solvents).

When enzymatic hydrolysis step B2 and alcoholic fermentation step C1 are carried out simultaneously in the same reactor, this constitutes the SSF process. The temperature is then about 35° C.

When enzymatic hydrolysis of the sugar polymers and fermentation of the glucose and xylose are carried out simultaneously, this constitutes the SSCF (simultaneous saccharification and co-fermentation) process. The temperature is then about 35° C.

Step C2 is the step for separation/purification of the product which can produce one or more alcohols and/or solvents that are ready for sale. This step advantageously comprises at least two sub-steps: a distillation step and a dehydration step.

Each of these various steps results in the production of a liquid phase, mixed with insoluble solid residues.

The process of the present invention thus proposes upgrading solid residues. It is thus necessary to separate them from the liquid phases. Said separation is carried out during the extraction step, in particular by pressing, centrifuging or filtration, as well as using any other technique which is known to the skilled person. The current limits for the solid/liquid separation equipment results in the presence of a portion of the liquid phase in the extracted cake which is in the range 25% to 80% by weight.

The step for extracting solid residue may be carried out after the enzymatic hydrolysis step B2 and before the fermentation step C1. In this case, the extracted cake comprises a liquid phase comprising 75% to 99% by weight of water, and sugars and also solid residues, including non-hydrolysed cellulose a portion of which may be recalcitrant, non-hydrolysed hemicelluloses, lignin and other insoluble compounds initially present in the substrate.

In accordance with one implementation of the process of the invention, the solid residue extraction step may be carried out between the fermentation step (step C1) and the separation/purification step (step C2). In this case, the extracted cake comprises a liquid phase comprising 75% to 99% by weight of water, alcohols and/or solvents (products) and unconverted sugars; and also solid residues comprising non-hydrolysed cellulose, a portion of which may be recalcitrant, non-hydrolysed hemicelluloses, lignin and other insoluble compounds initially present in the substrate, as well as a quantity of alcohol-producing microorganisms (in the range 2% to 20% depending on the enzymatic hydrolysis and alcoholic fermentation performances).

In accordance with another implementation, the solid residue extraction step is carried out after the separation/purification step (step C2). In this case, the extracted cake comprises a liquid phase comprising 80% to 99% by weight of water, unconverted sugars and traces of products (less than 0.1%); and also solid residues, comprising non-hydrolysed cellulose a portion of which may be recalcitrant, non-hydrolysed hemicelluloses, lignin and other insoluble compounds initially present in the substrate, as well as a small quantity of alcohol-producing microorganisms (in the range 2% to 20% depending on the enzymatic hydrolysis and alcoholic fermentation performances). The proportion of each component in this solid residue is a function of the initial substrate, the type of alkaline pre-treatment carried out and the operating conditions for enzymatic hydrolysis.

The proportion of each component in the extracted solid residue is a function of the initial substrate, the type of alkaline pre-treatment carried out and the operating conditions for enzymatic hydrolysis.

In the case of a Kraft type delignification pre-treatment, the quantity of lignin is in the range 2% to 40% by weight, more preferably in the range 3% to 30% by weight, the quantity of cellulose is in the range 15% to 85% by weight, preferably in the range 25% to 82% by weight, and the quantity of hemicelluloses is in the range 3% to 60% by weight, preferably in the range 5% to 50% by weight.

In the case of a partially delignified pre-treatment of the ARP type, the quantity of lignin is in the range 4% to 65% by weight, more preferably in the range 9% to 50% by weight, the quantity of cellulose is in the range 12% to 80% by weight, preferably in the range 20% to 70% by weight and the quantity of hemicelluloses is in the range 3% to 60% by weight, preferably in the range 5% to 45% by weight.

In the case of a non-delignifying alkaline pre-treatment, such as AFEX, for example, the quantity of lignin is in the range 15% to 70%, more preferably in the range 20% to 55%, the quantity of cellulose is in the range 4% to 50%, preferably in the range 10% to 45%, and the quantity of hemicelluloses is in the range 5% to 50%, preferably in the range 12% to 40%.

Advantageously, the cake may be washed in order to recover sugars and/or products trapped in the liquid phase. The liquid phase from the cake obtained after washing essentially contains water, and the solid phase is not or is only slightly modified.

During step D, a fraction of the solid residues undergoes acid digestion in the presence of an acid solution comprising a strong acid preferably selected from sulphuric and phosphoric acid, for a time in the range 10 minutes to 3 hours, at a temperature in the range 105° C. to 240° C., with an acid/solid material (SM) ratio in the range 0.1% to 100%, preferably in the range 0.5% to 70% and more preferably in the range 0.25% to 30%.

In accordance with one implementation of the process of the invention, the acid used during step D is a fraction of the pH correcting solution used during step B1.

The solid residue fraction sent to step D represents 15% to 100% by weight of the total quantity of extracted solid residues, preferably in the range 20% to 90% by weight and more preferably in the range 50% to 80% by weight.

The acid digestion step is carried out in one or more steps.

In a first implementation, the acid digestion step D is carried out in a single step.

At the end of this step, more than 20% by weight, preferably more than 70% by weight and still more preferably more than 90% by weight of the hemicelluloses contained in the solid residues are hydrolysed. A small proportion corresponding to less than 10% by weight, preferably less than 5% by weight and more preferably less than 2% by weight, is degraded.

A fraction of the cellulose is also hydrolysed, but in a smaller quantity than the hemicellulose fraction. Preferably, less than 20% by weight of the cellulose, preferably less than 10% and more preferably in the range 2% to 3% by weight, is degraded.

In accordance with another implementation of the process of the present invention, acid digestion step D is carried out in several successive cooking steps. It is then possible to vary the cooking conditions for each of the steps. During one of these steps, it is possible to select the acid digestion conditions so as to allow intense hydrolysis of the cellulose which is recalcitrant to enzymatic hydrolysis.

When the acid digestion step is carried out in several steps, a separation step is advantageously carried out between each cooking step to separate the liquid phase from the solid residue. Each separated liquid fraction is then recycled to step B.

At least a portion of the product from the acid digestion (step D) is recycled to step B. Advantageously, it is used to participate in the step for adjusting the pH (step B1) necessary in order to carry out the enzymatic hydrolysis.

The invention will now be described with reference to FIGS. 1 and 2.

Stations A to D shown in the figures respectively correspond to the various steps of the process of the present invention, designated by identical letters.

The function of station A is dependent on the alkaline pre-treatment under consideration.

In the case of a pre-treatment known as Kraft pre-treatment, the biomass is introduced into the cooking reactor or digester (A1) via a line 1. An alkaline solution, also termed white liquor, is also introduced into it via the line 2. The biomass is partially delignified by cooking at high temperature and in the presence of sodium hydroxide. The dissolved lignin is removed with the alkaline solution and is evacuated via the line 3 with the spent alkaline solution, also termed black liquor.

This delignification step may be carried out in several successive digesters, not shown in the figures, and is controlled by the operating parameters set for these devices.

The pulp obtained from the outlet from the digesters moving in the line 4 is enriched in cellulose: it contains in the range 60% to 90% by weight of cellulose with respect to the total solid material. It is sent to the reactor A2 to undergo a washing step: one or more washing liquids may be introduced via a line 5. The spent washing liquids are withdrawn via the line 6.

In the case of an AFEX treatment, the biomass is introduced via the line 1 into a cooking reactor (A1). An ammoniacal solution is introduced via the line 2 at a pressure of 15 to 30 bars, at a moderate temperature (70° C. to 110° C.). The mixture is held under these conditions for a predetermined time as a function of the substrate, then is depressurized at the digester outlet. The ammoniacal solution is recovered via the line 3 in the form of a gas for recycling. The pre-treated substrate extracted via the line 4 of the digester essentially has the same composition as the inlet substrate. The washing step A2 after this pre-treatment may be limited to a dilution step with a diluting liquid being introduced via the line 5, in which case the stream of washing liquid evacuated via the line 6 is zero.

In the case of an ARP pre-treatment, the biomass is introduced via the line 1 into the cooking reactor (A1). An ammoniacal solution is percolated over the biomass under pressure (15 to 30 bar) and at high temperature, 130° C. to 190° C. The biomass is partially delignified, a portion of the hemicelluloses is also dissolved. The sugars and the dissolved lignin are withdrawn with the spent alkaline solution and are evacuated via the line 3. The pre-treated substrate from cooking extracted via the line 4 is washed in a washing reactor (A2): one or more washing liquids may be introduced via the line 5. The spent washing liquids are removed via the line 6.

The pre-treated substrate, which may have been washed, which is obtained thereby and moves in the line 7, comprises in the range 50% to 95% by weight of water-insoluble material, more particularly in the range 60% to 85% by weight of water-insoluble material.

The pH adjusting step is carried out at station B1 by introducing a pH correcting solution via the line 8.

The pH has to be adjusted until an optimized pH in the range 4.5 to 5.5 is obtained, preferably in the range 4.8 to 5.2, for the enzymatic hydrolysis step.

Enzymatic hydrolysis is carried out on a pre-treated substrate which contains in the range 1% to 50% by weight of dry matter (insoluble initially, then dissolved by enzymatic action), preferably in the range 7% to 30%, more preferably in the range 10% to 25%.

The enzymes necessary for said step B2 are introduced via the line 9. The hydrolysate obtained after enzymatic hydrolysis is introduced into the fermentation reactor C1 via the line 10. Fermentation is carried out by yeasts or other microorganisms introduced into the reactor via the line 11.

Step C1 is followed by a separation/purification step C2 at the end of which the desired product or products (alcohols and/or solvents) obtained are extracted via the line 12, and the vinasses are extracted via the line 13.

The solid residue obtained after the preceding steps is evacuated via the line 14.

In FIG. 1, this line is represented in a non-limiting manner as originating from station C.

A fraction 14a of solid residue is sent to the acid digestion reactor D in which an acid solution is introduced via the line 15.

The fraction 14b which is not sent to the acid digestion reactor is extracted with a view to upgrading its material, for example for energy recovery by combustion.

A fraction of the product obtained after acid digestion is sent via the line 16 to the station B where the pH adjustment and enzymatic hydrolysis are carried out. This fraction represents less than 60% by weight, preferably less than 35% by weight.

The other fraction, which may be identical or modified by a solid/liquid separation operation, is evacuated via the line 17.

In a particular implementation, all of the product obtained after the acid digestion step is sent to the station B.

Because of the process of the present invention, the susceptibility to enzymatic hydrolysis of the solid phase of the acid product moving in the line 16 is greater than or equal to that of the residue 14 before acid digestion.

Figure 2:
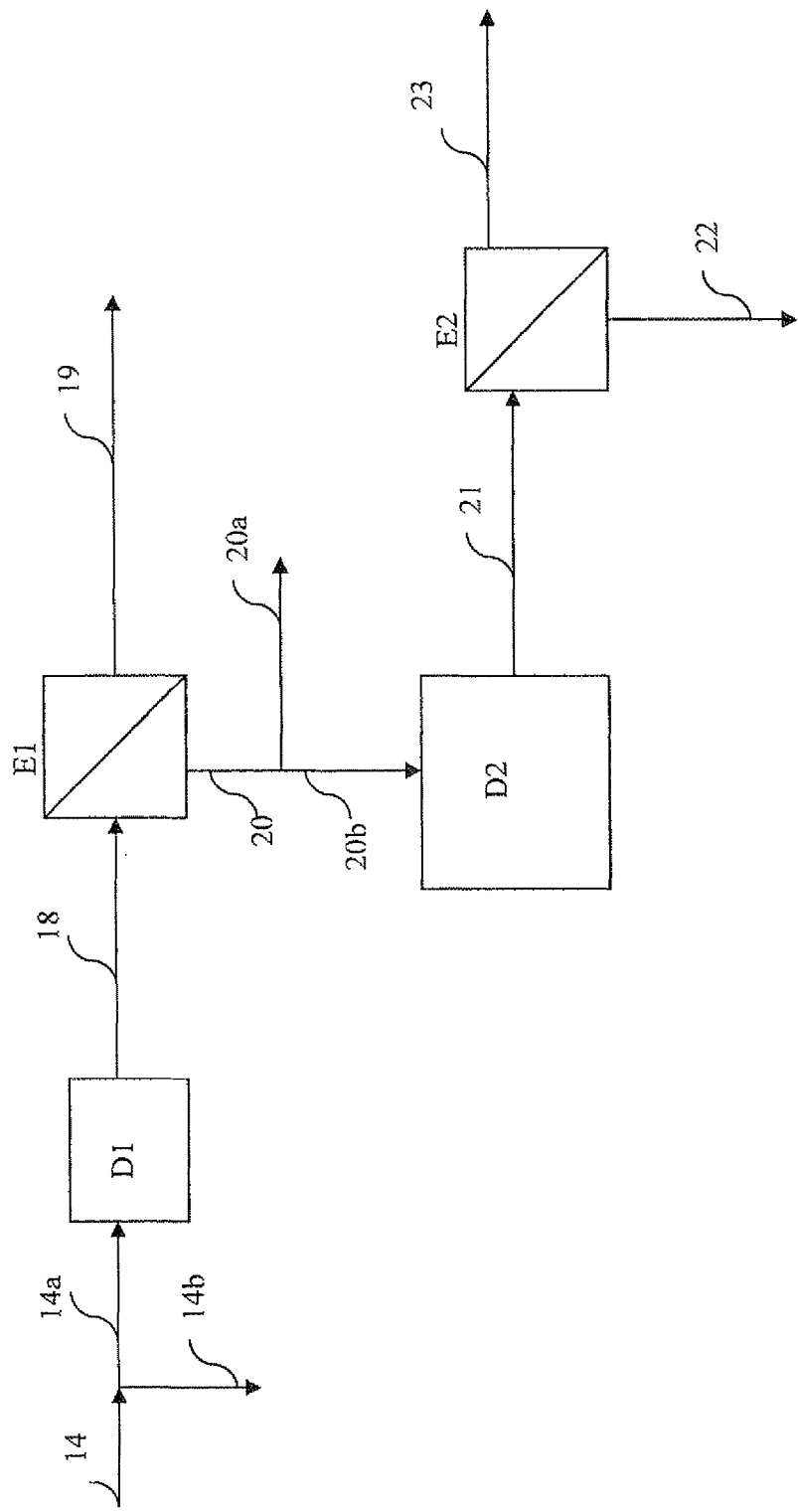
FIG. 2 is a diagrammatic representation of an implementation of multi-step acid digestion in accordance with the present invention.

In the implementation shown in FIG. 2, the acid digestion may advantageously be carried out in several steps.

A fraction 14a of the solid residue is sent to a first cooking reactor D1 operating under mild conditions. The product obtained is evacuated via the line 18 to a separator E1. At the separator outlet, a liquid phase comprising hydrolysed hemicelluloses is withdrawn via the line 19, which may be recycled and returned to the station B, and a solid residue containing cellulose is evacuated via the line 20.

Advantageously, a portion of the solid residue is withdrawn directly via the line 20a since the cellulose of said insoluble fraction has a retained or even substantially improved enzymatic digestibility and is thus more accessible to cellulolytic enzymes.

The other portion 20b is sent to a second cooking reactor operating under more severe conditions than the reactor D1, to carry out intense hydrolysis of the cellulose.

The product obtained after this second acid digestion step D2 is sent via a line 21 to a second separator E2. Thence, from the outlet from E2, a liquid phase is withdrawn via the line 23, and may advantageously be recycled to the station B along with a solid residue withdrawn via the line 22 which is highly depleted in cellulose. As already mentioned, a small proportion of this insoluble cellulose is more accessible to cellulolytic enzymes and may also be recycled to the station B.

Thus, by carrying out acid digestion in several steps, it becomes possible to withdraw a substantially improved quantity of cellulose from the solid residue, and as a result improve upgrading thereof.

Recycling non-hydrolysed polysaccharides means that the total weight yield of the process can be increased. Advantageously, this gain in yield may be carried out without increasing the quantity or flow rate of the chemical products employed, particularly the acids. Finally, the more intense hydrolysis of the pentoses of the cake can if necessary compensate for the lower enzymatic hydrolysis of pentoses, and thus can avoid the accumulation of pentoses in the cake which may appear in a conventional recycle.

EXAMPLES

Example 1 (Not in Accordance with the Invention)

A process for the production of ethanol from wood is considered, in which the wood is pre-treated in a Kraft type papermaking process, which is an alkaline process carried out in the presence of sodium hydroxide. The lignin-depleted pulp from the Kraft process is then washed and neutralized, then introduced into the process for the conversion of cellulosic substrate to ethanol by enzymatic hydrolysis and fermentation of glucose.

The process treated 100 tonnes/hour of wood with 20% moisture content. The composition of the dry matter was as follows:

| | |
|---|---|
| Cellulose | 46.3% |
| Hemicelluloses | 17.0% |
| Acetate | 0.7% |
| Lignin | 29.0% |
| Ash | 3.5% |
| Others | 3.5% |

The Kraft process was operated under conditions such that the paper pulp at the outlet contained:

| | |
|---|---|
| 98.0% | initial cellulose |
| 65.0% | initial hemicelluloses |
| 100.0% | initial acetate |
| 5.0% | initial lignin |
| 80.0% | initial ash |
| 80.0% | other initial compounds |

The flow rate of the paper pulp at the outlet from the Kraft process was thus 51.3 tonnes/hour of dry matter.

The washing process was such that the washed pulp had a pH of 9.0 and contained 13% of solid material.

The process for conversion to ethanol contained the following steps: enzymatic hydrolysis, alcoholic fermentation, separation of solid residues, and distillation and dehydration of ethanol. The enzymatic hydrolysis was operated at a pH of 4.8. for this reason, the acid consumption 8 to rectify the pH of the paper pulp was 8880 N. Under the selected hydrolysis conditions, the enzymatic hydrolysis yield for the cellulose was 65%, while that for the hemicelluloses was 35% and the fermentation yield was 95% of the theoretical maximum. The process produced 12.27 tonnes/hour of 99.7% ethanol and 54.67 tonnes/hour of solid cake containing 40% solid material.

Example 2 (In Accordance with the Invention)

Here we describe the implementation of the invention in the process described in Example 1. Thus, 50 tonnes/hour of cake product was sent to an acid digestion reactor. Acid digestion was carried out at 150° C. for one hour in the presence of $H_2SO_4$. The quantity used here was 20 g $H_2SO_4$/kg of solid material (2% by weight). Acid hydrolysis resulted in conversion of all of the hemicelluloses into C5 sugars, with a 3% degradation into furfural. 90% of the C5 and C6 sugars present in the cake at the start of acid hydrolysis were respectively converted into furfural and 5-hydromethyl furfural. The substrate from the acid hydrolysis was mixed with washed pulp before the neutralization step, thus supplying 8412 N; the complementary supply of acid to bring the mixture to the pH for hydrolysis was 468 N. The yields for the process for the conversion of substrate into ethanol were retained, and so the ethanol production was 15.95 tonnes/hour, i.e. an increase in the overall yield of the process of 30%, for the same consumption of wood (80 tonnes/hour of dry matter) and acid (8880 N).

Example 3 (Not in Accordance with the Invention)

A process for the production of an acetone-butanol-ethanol mixture from straw is considered.

The straw was conditioned then treated in a process known as an AFEX process, which consists of impregnating the straw with ammonia under pressure, followed by explosive depressurization. The substrate was then washed and neutralized before being introduced into a process for the production of acetone-butanol-ethanol by enzymatic hydrolysis, separation of the solid residue then fermentation of the sugars derived from the cellulose and hemicelluloses (C5 and C6).

The process treated 150 tonnes/hour of wood with 15% moisture content. The composition of the dry matter was as follows:

| | |
|---|---|
| Cellulose | 40.0% |
| Hemicelluloses | 27.0% |
| Acetate | 0.7% |
| Lignin | 23.0% |
| Ash | 6.0% |
| Others | 3.3% |

The AFEX process was operated under conditions such that the substrate at the outlet had the same composition and the same flow rate as the substrate at the inlet. All of the ammonia was extracted from the substrate. The substrate thus had a neutral pH at the end of pre-treatment. The substrate was then taken up into suspension before undergoing enzymatic hydrolysis, the pH of the solution being adjusted to a pH of 5 for this step, which meant that the acid consumption was 9350 N. The hydrolysis was carried out under conditions that could produce 85% hydrolysis of the cellulose and 70% hydrolysis of the hemicelluloses.

After separating the residual solid, 53.5 tonnes/hour of solid material, fermentation of the sugars produced 33 g of ABE mixture per 100 g of sugars (glucose+xylose), i.e. a flow rate of 22.2 tonnes/hour of ABE.

Example 4 (In Accordance with the Invention)

Implementation of the invention for the process described in Example 3 will be described here.

Thus, 16.5 tonnes of solid material/hour of cake produced was sent to an acid digestion reactor. The quantity was limited to maintain 25% of cellulose+hemicellulose in the composition of the cake. The acid digestion was carried out at 150° C. for 40 minutes in the presence of $H_2SO_4$. The quantity employed here was 36 g of $H_2SO_4$/kg of solid material (3.6% by weight). The acid hydrolysis resulted in a conversion of 85% of the hemicelluloses into C5 sugars plus a degradation of 7% into furfural. 70% of the C5 and C6 sugars present in the cake at the start of the acid hydrolysis was respectively converted into furfural and 5-hydromethyl furfural. The substrate from the acid hydrolysis was mixed with the washed pulp before the neutralization step, thereby providing 9183 N; the complementary supply of acid to bring the mixture to the pH for hydrolysis was 167 N.

The yields for the process for conversion of substrate into ABE were retained, and the ABE production was thus 23.7 tonnes/hour, i.e. an increase in the overall yield of the process of 7%, for the same consumption of straw (150 tonnes/hour of dry matter) and acid (9350 N).

Example 5 (In Accordance with the Invention)

An implementation of a variation of the invention in the process described in Example 3 will be described here.

Thus, 85% of the cake produced was sent to a two-stage acid digestion reactor. The first digestion was carried out at 135° C. for 90 minutes in the presence of $H_2SO_4$, then a solid-liquid separation was carried out. The second digestion was carried out at 200° C. for 80 minutes. The quantity employed here was 20 g of $H_2SO_4$/kg of solid material (2% by weight) for the first digestion and 150 g of $H_2SO_4$/kg of solid material (15% by weight) for the second digestion. The first acid hydrolysis step resulted in a conversion of 85% of hemicelluloses into C5 sugars plus a degradation of 2% into furfural; the second step converted 80% of the cellulose into glucose. 75% of the C5 and C6 sugars present in the cake at the start of acid hydrolysis were respectively converted into furfural and 5-hydromethyl furfural and into degradation products of the latter. The liquid substrate from the acid hydrolysis steps was mixed with the washed pulp before the neutralization step, thereby providing 115310 N. A basic pH corrector (105960 N) was mixed with this stream to bring the mixture to the pH for hydrolysis.

The presence of glucose in the substrate at the inlet to the enzymatic hydrolysis step reduced the yield for this hydrolysis slightly because of inhibition by their enzyme product, and so this yield was 80% (and not 85% under the same conditions in the absence of glucose).

The yields for the fermentation of sugars into ABE were retained, and the ABE production was thus 25.5 tonnes/hour, i.e. an increase in the overall yield of the process of 15%, for the same consumption of straw (150 tonnes/hour of dry matter).

The invention claimed is:

1. A process for the production of alcohols and/or solvents from a cellulosic or lignocellulosic substrate, comprising:
   A. pre-treating said substrate with an alkali, comprising:
      Step A1: heating the substrate in the presence of an alkaline chemical reagent and
      Step A2: optionally washing the alkaline-treated substrate,
      wherein the alkaline pre-treatment conditions are carried out at a temperature in the range of 1513° C. to 175° C. for a period in the range 1 to 7 hours in the presence of NaOH and sodium sulphate, whereby at least one pre-treated substrate is obtained;

B. hydrolyzing the pre-treated substrate, comprising
    Step B1: adjusting the pH of the pre-treated substrate to between 4.5 and 5.5 and
    Step B2: enzymatically hydrolyzing the pre-treated substrate using cellulolytic and/or hemicellulolytic enzymes,
    whereby a hydrolysate comprising a liquid phase containing sugars and a solid residue is obtained;
C. producing alcohols and/or solvents from the hydrolysate comprising:
    Step C1: fermenting the hydrolysate with a microorganism capable of producing alcohols or solvents from the hydrolysate to produce a solution of alcohols and/or solvents and a solid residue;
    Step C2. separating and purifying the products of the fermentation of step C1, whereby one or more purified alcohols and/or solvents are obtained and separated from the solid residue;
    Step C3. extracting the solid residue, conducted after step B2, C1 and/or C2;
D. digesting with an acid at least a fraction of the extracted solid residue, wherein the acid digestion is carried out at a temperature in the range 105° C. to 240° C. for a period in the range 10 minutes to 3 hours in the presence of an acid solution comprising a strong acid, with an acid/solid material (SM) ratio in the range 0.1% to 100%, and recycling a portion or all of the thus-obtained digestion product to step B.

2. The process of claim 1, wherein adjusting the pH of step B1 and the enzymatic hydrolysis of step B2 are carried out simultaneously in the same reactor.

3. The process of claim 1, wherein the solid residue is extracted after the enzymatic hydrolysis step B2 and before the fermentation step C1.

4. The process of claim 1, wherein the solid residue is extracted between the fermentation step C1 and the separation/purification step C2.

5. The process of claim 1, wherein the solid residue is extracted after the separation/purification step C2.

6. The process of claim 1, wherein the fraction of solid residue sent to the acid digestion reactor in D represents in the range 15% to 100% by weight of the total quantity of extracted solid residues, preferably in the range 20% to 90% by weight and more preferably in the range 50% to 80% by weight.

7. The process of claim 1, wherein the acid digestion step D is repeated at least once on the digestion product prior to it being recycled to step B.

8. The process of claim 7, further comprising a step of separating the liquid fraction from the solid residues of the acid digestion product prior to any subsequent acid digestion steps to the solid residue.

9. The process of claim 8, wherein each separated liquid fraction is recycled to step B.

10. The process of claim 1, wherein the acid is sulphuric acid or phosphoric acid.

11. The process of claim 1, wherein the portion or all of the thus-obtained digestion product is recycled to the step of adjusting the pH in step B1.

* * * * *